United States Patent
Lange et al.

(10) Patent No.: US 9,519,650 B2
(45) Date of Patent: Dec. 13, 2016

(54) SYSTEMS AND METHODS FOR GENETIC DATA COMPRESSION

(75) Inventors: Christoph Lange, Cambridge, MA (US); Dandi Qiao, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 172 days.

(21) Appl. No.: 14/131,084

(22) PCT Filed: Jul. 6, 2012

(86) PCT No.: PCT/US2012/045715
§ 371 (c)(1),
(2), (4) Date: Apr. 10, 2014

(87) PCT Pub. No.: WO2013/006776
PCT Pub. Date: Jan. 10, 2013

(65) Prior Publication Data
US 2014/0214780 A1 Jul. 31, 2014

Related U.S. Application Data (60) Provisional application No. 61/504,838, filed on Jul. 6, 2011.

(51) Int. Cl.
*G06F 17/30* (2006.01)
*G06F 19/18* (2011.01)

(52) U.S. Cl.
CPC ......... *G06F 17/30153* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 6,253,264 B1 * | 6/2001 | Sebastian | G06T 9/005 341/107 |
| 8,340,914 B2 * | 12/2012 | Gatewood | H03M 7/3084 702/19 |

(Continued)

FOREIGN PATENT DOCUMENTS

WO   WO 03031565 A2 *   4/2003   ............. G06F 19/22

OTHER PUBLICATIONS

Antoniades, A. et al., "A Binary format for genetic data designed for large whole genome studies that enable both marker and strand based analyses," [8th IEEE International Conference on BioInformatics and BioEngineering (BIBE)] Oct. 2008, pp. 1-4, available online at http://www.medinfo.cs.ucy.ac.cy/doc/Publications/Conferences/2008/2008_A_Binary_Format_for_Genetic_Data_Designed_for_Large_Whole_Genome_Studies_that_Enable_Both_Marker_and_Strand_Based_Analyses.pdf. (last accessed on Jan. 6, 2014).

(Continued)

*Primary Examiner* — Richard Bowen
(74) *Attorney, Agent, or Firm* — Morgan, Lewis & Bockius LLP (57) ABSTRACT

Genetic data may be compressed efficiently by selecting for each bi-allelic marker, from among multiple compression algorithms with different associated storage requirements that depend on the minor allele frequency of the respective marker, the algorithm that has the lowest storage requirements. Efficient approaches compress, store, and load pedigree file data. A hybrid method is used that selects between multiple alternative compression algorithms whose performance depends on the frequency of certain observable genetic variations. The hybrid method may achieve higher compression ratios than PLINK or PBAT. Further, it results in a compressed data format that, generally, does not require any overhead memory space and CPU time for decompres- (Continued)

sion, and, consequently, has shorter loading times for compressed files than the binary format in PLINK or PBAT. Moreover, the compressed data format supports parallel loading of genetic information, which decreases the loading time by a factor of the number of parallel jobs.

11 Claims, 5 Drawing Sheets

(56) References Cited

U.S. PATENT DOCUMENTS

| | | | |
|---|---|---|---|
| 2002/0073405 A1* | 6/2002 | Chilimbi | G06F 8/4442 717/151 |
| 2002/0097172 A1* | 7/2002 | Fallon | G06T 9/00 341/51 |
| 2002/0101367 A1* | 8/2002 | Geiger | H03M 7/30 341/51 |
| 2007/0180333 A1* | 8/2007 | Thekkath | G06F 11/3636 714/45 |
| 2008/0287308 A1 | 11/2008 | Hubbell et al. | |
| 2010/0011012 A1* | 1/2010 | Rawson | H04L 67/30 707/E17.009 |
| 2011/0093208 A1 | 4/2011 | Wang et al. | |
| 2011/0167173 A1* | 7/2011 | Bansal | H03M 7/30 709/247 |
| 2011/0295858 A1* | 12/2011 | Ahn | G06F 17/30985 707/741 |
| 2011/0320418 A1* | 12/2011 | Luo | H03M 7/30 707/693 |
| 2012/0102263 A1* | 4/2012 | Aswadhati | G06F 13/16 711/103 |
| 2012/0173496 A1* | 7/2012 | Hodgens | G06F 17/30501 707/693 |
| 2012/0296883 A1* | 11/2012 | Ganesh | G06F 17/30315 707/693 |
| 2012/0330567 A1* | 12/2012 | Bauer | G06F 19/22 702/20 |
| 2013/0073217 A1* | 3/2013 | Dewey | G06F 19/24 702/20 |

OTHER PUBLICATIONS

Kozanitis, C. et al. "Compressing Genomic Sequence Fragments Using SlimGene," J. Comput Biol., vol. 18, No. 3., pp. 401-413 (Mar. 2011).

Qiao, D. et al. "Handling the data managment needs of High-throughput sequencing data: SpeedGene, a compression algorithm for the efficient storage of genetic data," BMC Bioinformatics, vol. 13, No. 100, pp. 1-7 (May 16, 2012).

International Search Report for International Application No. PCT/US2012/045715, issued Nov. 28, 2012 and mailed Dec. 17, 2012.

* cited by examiner

FIG. 1

```
ped - Notepad
File   Edit   Format   View   Help
A1  A2  A3  A4  A5  A6              130
 1   1   0   0   1   2  | 1 2 3 3 2 4 3 |  1 0 0 2 2
 1   8   0   0   2   1  | 2 2 2 3 0 0 3 |  1 2 2 2 3
 1   3   1   2   1   2  | 1 2 3 2 2 2 3 |  3 1 1 2 3
 1   4   0   0   2   1    1 0 3 2 4 4 3    3 1 1 2 2
 1   5   0   0   1   2    1 2 3 3 2 4 3    1 0 0 2 2
 1   6   0   0   2   1    2 2 2 3 0 0 3    1 2 2 2 3
         110                      120
```

| 130 ↘ ALLELES | NUMBER OF MINOR ALLELES | BINARY NUMBER |
|---|---|---|
| 1 2 \| 3 3 \| 2 4 \| 3 1 | 1 0 1 1 | 01 \| 00 \| 01 \| 01 |
| 2 2 \| 2 3 \| 0 0 \| 3 1 → | 2 1 3 1 → | 10 \| 01 \| 11 \| 01 |
| 1 2 \| 3 2 \| 2 2 \| 3 3 | 1 1 2 0 | 01 \| 01 \| 10 \| 00 |

8 CHAR + 8 SPACES = 16 BYTES        8 BITS = 1 BYTE

SYSTEMS AND METHODS FOR GENETIC DATA COMPRESSION

CROSS-REFERENCE TO RELATED APPLICATION

This application is a U.S. National Phase Application of PCT/US2012/045715, filed Jul. 6, 2012, which claims priority to and the benefit of U.S. Provisional Patent Application No. 61/504,838, filed on Jul. 6, 2011, both of which are incorporated herein by reference.

GOVERNMENT SUPPORT

This invention was made with government support under R01MH081862, R01MH087590, U01HL089856 and U01HL089897 awarded by the National Institute of Health. The Government has certain rights in the invention.

TECHNICAL FIELD

The present invention relates to systems and methods for compressing genetic data.

BACKGROUND

Genome-wide association studies (GWAS) are now a standard tool that is accessible (in terms of cost and laboratory efforts) for research groups, resulting in imminent demand for high-throughput sequencing data. As a result, the data-management requirements for analysis have changed fundamentally. During the days of candidate gene analyses and linkage analysis, "only" up to several thousands of genetic loci had to be stored and loaded into analysis packages, whereas current GWAS provide genetic information on several million genetic loci. For high-throughput sequencing studies, the number of genetic loci will again increase by several magnitudes.

The standard data format to store genetic information for the analysis in software packages such as, e.g., FBAT, PBAT, or PLINK is the pedigree file type. Pedigree files contain the necessary family/pedigree information and genetic data for the genotyped loci in the study. The pedigree files are usually ASCII text files that are human-readable. However, for GWAS, such pedigree files are often impractically large, which creates not only storage challenges, but can also become a source for potential data management errors. The typical size of a pedigree file can be 1 Gigabyte to 30 Gigabytes for common-variants data (e.g., GWAS data), and can be up to several Terabytes for sequence data. Merely loading such large files can take up to a few hours. This results in great waste of disk space and computation time. Due to the popularity of genome-wide analysis, this problem is encountered routinely, and only a few alternatives are available. As high-throughput sequencing data becomes standard in research, the problem will grow even worse.

One possible solution is to use general-purpose compression software, such as gzip. However, such software is not designed specifically for genotype data and its analysis. Decompression is always needed whenever the data is accessed. Also, general-purpose compression software typically only achieves a compression factor of five to six, and does not support parallel processing. Several solutions that are better tailored to genetic data compression have been proposed. For example, the freely available PLINK and PBAT software packages, which are whole-genome association analysis toolsets, have introduced binary PED formats. This format ensures that only two bits are required for storing the information for one genotype. Furthermore, sophisticated compression techniques designed specifically for sequence data (e.g., DNAzip) have been proposed that can achieve excellent compression rates. However, these techniques generally require a reference human genome and a reference single-nucleotide polymorphism (SNP) map, which entails large storage overhead.

Accordingly, there is a need for more efficient compression and storage techniques tailored to genetic data.

SUMMARY

Described herein are various efficient approaches to compression, storage, and loading of pedigree file data. In various embodiments, a hybrid method is used that selects between multiple alternative compression algorithms whose performance depends on the frequency of certain observable genetic variations. The hybrid method may achieve higher compression ratios than PLINK or PBAT. Further, it results in a compressed data format that, generally, does not require any overhead memory space and CPU time for decompression, and, consequently, has shorter loading times for compressed files than the binary format in PLINK or PBAT. Moreover, the compressed data format supports parallel loading of genetic information, which decreases the loading time by a factor of the number of parallel jobs. Thus, the techniques described herein may enable the storage and analysis of next-generation sequencing data in existing hardware environments.

In a first aspect, the invention provides a computer-implemented method of compressing, for a plurality of subjects, genetic data corresponding to at least one bi-allelic marker having at least one minor allele frequency associated therewith. The genetic data may, prior to compression, be stored in ASCII format. The method utilizes two or more compression algorithms (e.g., in some embodiments, three), and involves computing (e.g., with a computer processor) storage requirements associated with each of the compression algorithms for each of the markers. The storage requirements of the compression algorithms depend on the minor allele frequency associated with the marker, as well as, in some embodiments, on the number of subjects and/or other factors. The algorithm further includes compressing the genetic data for each marker using the compression algorithm that has the lowest associated storage requirement, and storing the compressed genetic data (e.g., in system memory or on a hard drive or other non-volatile data storage medium). In addition, the compressed genetic data may be analyzed (generally without prior de-compression), and one or more user queries may be processed based on the compressed data. In some embodiments, the compressed genetic data is stored on a non-volatile data storage medium in binary format and, when loaded into memory for analysis, translated into integer format (e.g., an integer array). (This mere translation from one data format into another does not constitute decompression.)

In certain embodiments, the compression algorithms are selected from (i) a binary-encoding algorithm; (ii) an algorithm wherein total numbers and unique indices of all subjects having a rare homozygous genotype for a marker, all subjects having a heterozygous genotype for the marker, and all subjects having an unknown genotype for the marker are expressed in binary numbers; and (iii) an algorithm wherein the total numbers and unique indices of all subjects having a rare homozygous genotype for a marker and all subject having an unknown genotype for the marker are expressed in binary numbers, and the unique indices of all subjects having a heterozygous genotype for the marker are expressed in a single n-digit number, where n is the number of subjects.

In another aspect, a computer system for compressing genetic data is provided. The system includes one or more data storage media (e.g., system memory and/or one or more mass storage devices) for storing original genetic data for a plurality of subjects (the data corresponding to one or more bi-allelic markers with associated minor allele frequencies), as well as compressed genetic data. Further, the system includes a computer processor (in communication with the storage medium) for computing, for each of the bi-allelic markers, computer storage requirements associated with each of two or more compression algorithms (e.g., the three algorithms set forth above). The storage requirement of one or more of the compression algorithms depends, at least in part, on the minor allele frequency associated with the marker. The processor is further configured for compressing the genetic data for each of the bi-allelic markers using the compression algorithm having the lowest associated storage requirement. Further, it may be configured to analyze the compressed genetic data (optionally after translation into integer format) without prior decompression, and/or to process user queries based on the compressed genetic data. The compressed genetic data may be stored in binary format on the data-storage medium, and the computer processor may be configured to load the compressed genetic data into memory and convert the binary format into integer format prior to analyzing the data.

In a third aspect, the invention is directed to a computer-implemented method of compressing genetic data for a plurality of subjects and for one or more bi-allelic marker(s), where each subject is associated with a unique index. The genetic data may, prior to compression, be stored in ASCII format. The method involves using a computer processor to computationally determine from the genetic data (i) the total number and the unique indices of all subjects having a rare homozygous genotype for a marker, (ii) the total number and the unique indices of all subjects having a heterozygous genotype for the marker, and (iii) the total number and the unique indices of all subjects having an unknown genotype for the marker. The determined total numbers and unique indices of the subjects may be stored in computer memory or on another data storage medium (e.g., a hard drive), e.g., in binary format. The method may also include performing an analysis based on the stored total numbers and unique indices of the subjects.

In a further aspect, the invention is directed to a computer system for compressing genetic data. The system includes one or more data storage media for storing original genetic data for a plurality of subjects and for one or more bi-allelic marker(s) (each subject being associated with a unique index) and compressed genetic data, and a computer processor in communication with the data storage media. The processor computationally determines from the original genetic data (i) the total number and the unique indices of all subjects having a rare homozygous genotype for a marker, (ii) the total number and the unique indices of all subjects having a heterozygous genotype for the marker, and (iii) the total number and the unique indices of all subject having an unknown genotype for the marker; the compressed genetic data comprises the total numbers and unique indices of the subjects. The computer processor may be further configured to analyze the compressed genetic data without decompression (but, optionally, if the data is stored in binary format, after conversion into integer format upon loading the data into memory).

In a fifth aspect, the invention is directed to a computer-implemented method of compressing genetic data for n subjects (each being associated with a unique index) and for at least one bi-allelic marker. The method includes using a computer processor to computationally determine from the original genetic data (i) the total number and the unique indices of all subjects having a rare homozygous genotype for a marker, (ii) the total number and the unique indices of all subjects having an unknown genotype for the marker, and (iii) the unique indices of all subject having a heterozygous genotype for the marker. The method further involves storing the total numbers and unique indices of the subjects having the rare homozygous genotype and the subjects having the unknown genotype as binary numbers in computer memory, and storing a binary number of n digits indicating the indices of the subjects having the heterozygous genotype in computer memory or on another data storage medium (e.g., a hard drive). The method may also include performance of an analysis based on the stored total numbers and unique indices of the subjects having the rare homozygous genotype and the subjects having the unknown genotype and on the binary number of n digits indicating the indices of the subjects having the heterozygous genotype.

In yet another aspect, the invention is directed to a computer system for compressing genetic data; the system includes one or more data storage media for storing both original genetic data for a plurality of n subjects and for at least one bi-allelic marker and compressed genetic data, and a computer processor in communication with the data storage media. The processor is configured to computationally determine from the original genetic data (i) the total number and the unique indices of all subjects having a rare homozygous genotype for a marker, (ii) the total number and the unique indices of all subjects having an unknown genotype for the marker, and (iii) the unique indices of all subject having a heterozygous genotype for the marker. The compressed genetic data includes (i) binary numbers for the total numbers and unique indices of the subjects having the rare homozygous genotype and the subjects having the unknown genotype and (ii) a binary number of n digits indicating the indices of the subjects having a heterozygous genotype. The computer processor may further be configured to analyze the compressed genetic data without decompression (but, optionally, if the data is stored in binary format, after conversion into integer format upon loading the data into memory).

BRIEF DESCRIPTION OF THE DRAWINGS

In the foregoing can be more readily understood from the following detailed description, in particular, when taken in conjunction with the drawings, in which.

DESCRIPTION

1. Genetic Data Format

Figure 1:
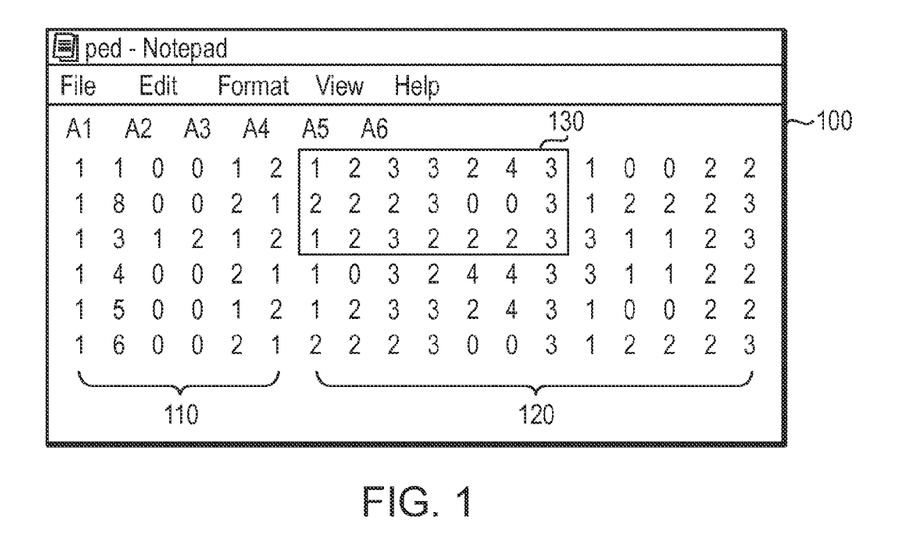
FIG. 1 is a screen shot illustrating an example of a pedigree file in the LINKAGE format in accordance with various embodiments.

Algorithms in accordance herewith may be used to compress data stored in pedigree files, i.e., human-readable text files that store, for a (typically large) number of individuals (or "subjects"), their genetic information for various markers—i.e., DNA sequences at known locations within a chromosome that include observable genetic variations—along with their family relationships and an indication of the presence or absence of a particular trait or disease. Pedigree files are often provided in the LINKAGE format, which has the general text structure shown in the example of FIG. 1. The first line 100 usually contains the marker names, separated by a space character. Starting from the second line, each line includes pedigree and genetic information for each individual. The first six columns 110 of these lines specify each individual's pedigree information in the order of pedigree ID, subject ID, father ID, mother ID, sex, and affection status. The subject ID must be unique within one's family. Father and mother ID are 0 if this information is unknown, as is the case, e.g., in a population-based study of unrelated subjects. Sex is "1" for male and "2" for female. Affection status is "1" if the subject is unaffected (i.e., does not have the disease or trait of interest), "2" if affected, and "0" if the status is unknown. The other columns 120 contain the genetic data for each individual, separated by a space between each marker. Information for each marker is represented by two columns for two alleles, also separated by a space. The allele information is coded using numerals 0 to 4 where "1"=A, "2"=C, "3"=G, "4"=T, and "0" means missing allele information.

The LINKAGE format is the most commonly used pedigree file format, and will be used to illustrated compression algorithms in accordance with various embodiments. However, the algorithms described herein are also straightforwardly applied to any other pedigree file format (including, e.g., long-format), as well as to HapMat format.

2. Compression Algorithms

Various embodiments utilize one or a combination of three different compression algorithms whose performance depends on the minor allele frequency (MAF) of the genetic locus to be stored. Depending on the MAF, a "hybrid" or optimization algorithm may select for each marker the best procedure among the three compression algorithms. The first algorithm is based on the binary format implemented in PLINK and PBAT. It utilizes the fact that the marker information for each marker can be represented using a two-digit binary number. The second algorithm uses subject indices to indicate heterogeneous, homogeneous, and missing genotypes. The third algorithm uses binary digits to indicate heterogeneous genotype, and subject indices to indicate homozygous and missing genotypes. For all three compression algorithms, the required memory space for storage can be computed prior to compression. This allows the hybrid algorithm to select the optimal method before compressing the data. The three different compression algorithms are described in detail in the following sections.

2.1 Algorithm I: Compression Using Binary Encoding

Figure 2:
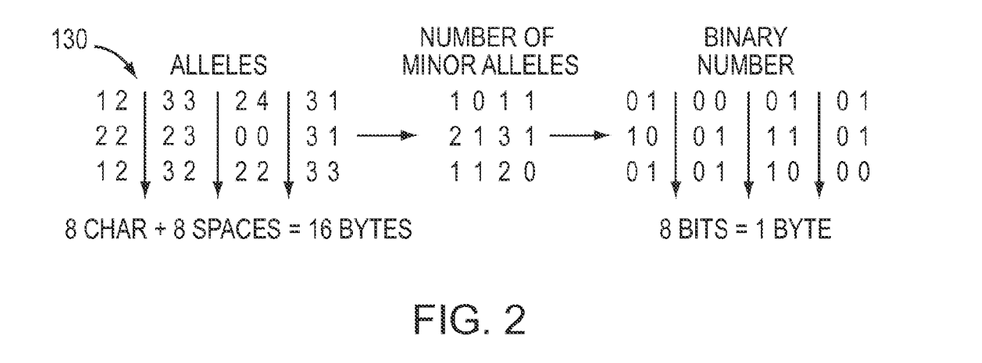
FIG. 2 is an illustration of a compression algorithm using binary encoding in accordance with various embodiments.

For any pedigree file, we assume that there are only bi-allelic markers in the file. Then, for any allele of a marker, an individual can only have zero, one, or two of this allele. Also, the allele information can be missing for any individual at any marker. Thus, the marker information can be transformed into the number of the copies of a certain allele which is zero, one, two, or missing. The four different possibilities can be represented by a two-digit binary number. In the compression process, in one embodiment, the minor alleles are determined for each marker, and "00," "01," and "10" are used to represent zero, one, or two copies, respectively, of the minor allele at that marker. Further, "11" is used to indicate that the genetic information is missing at this marker for the individual. Thus, information for one marker and one individual in the original file can be converted into two binary digits, i.e., two bits. Four of such two-digit binary numbers sum up to eight bits, which equals one byte. Therefore, the genetic information of four markers for one individual can be converted into one byte in a binary file. FIG. 2 illustrates this binary-encoding compression algorithm as applied to the genetic information 130 of the first four markers for the first three individuals in the example of FIG. 1. The minor alleles for the first four markers are 2, 2, 2, and 1, respectively.

Based on this conversion method, the genetic information in the pedigree file can be compressed into a much smaller binary file. As shown in the example of FIG. 2, the genetic information for four genotypes occupies 16 bytes in the original pedigree file, and is converted to only one byte in the compressed file, which may save up to a factor of 16 of disk space. For the purpose of efficient loading, the information of all the subjects for one marker may be compressed together. Further, the major and minor allele types may be stored along with the compressed data to facilitate retrieving the genotype data at a later time, should this be desired. If the number of subjects is not a multiple of four, 1's may be padded to the end of the last character for this marker. Saving the allele types and padding both decrease the compression factor of sixteen by a small amount. In addition, since the pedigree information is saved in a separate text file, the space taken up by the pedigree information itself is generally not compressed. However, because the space occupied by the pedigree information, allele types, and the padded bits is much smaller than the space taken by the genetic information, the algorithm can still compress the original file by a factor of approximately 16. If there are n subjects in the dataset, the storage requirement per marker for this algorithm is given by:

$$[2 \times n/8] \text{Bytes} \quad (1).$$

2.2 Algorithm II: Compression Using Subject Indices

Figure 3A:
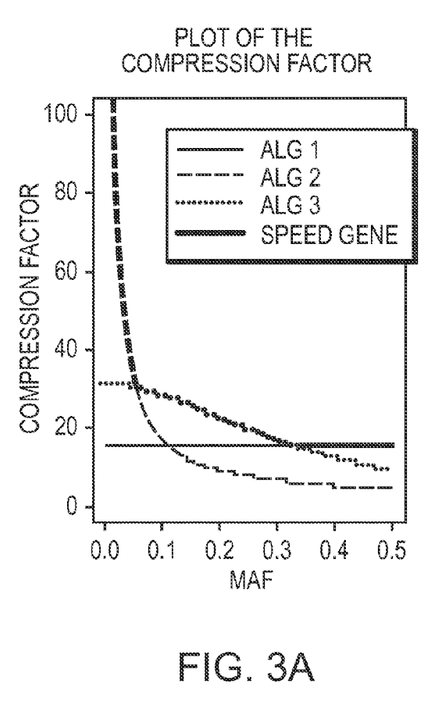
FIGS. 3A and 3B show plots comparing the compression factors and the bits needed for storing one genotype information, respectively, for three algorithms in accordance with various embodiments.
Figure 3B:
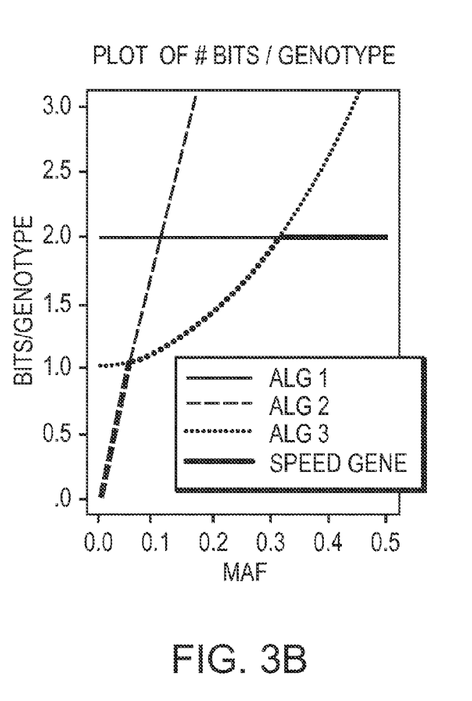
Figure 4A:
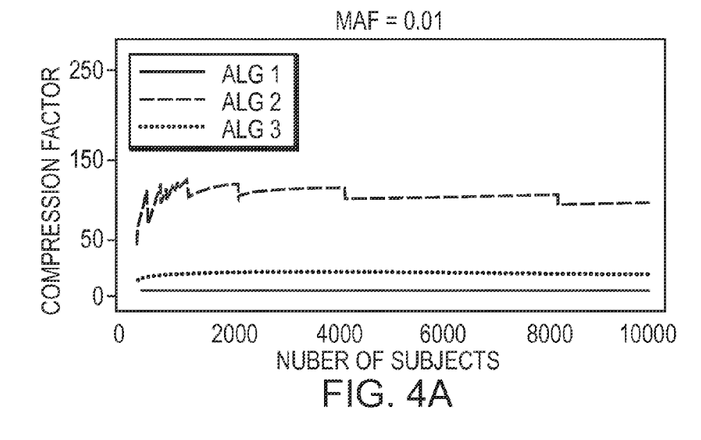
FIGS. 4A-4H show plots comparing the compression factors versus the number of subjects included for one SNP
Figure 4B:
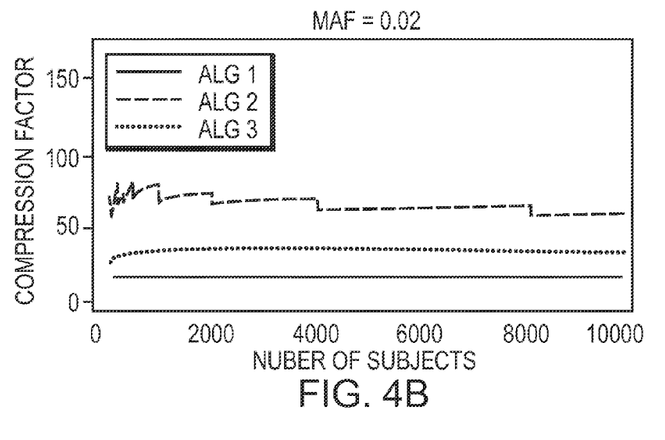
Figure 4C:
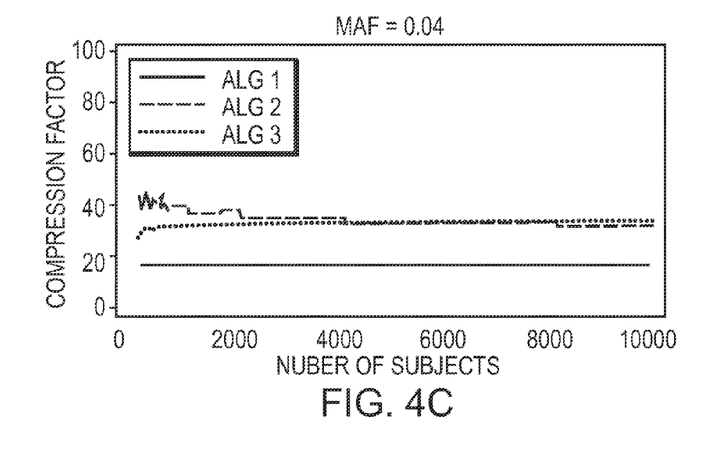
Figure 4D:
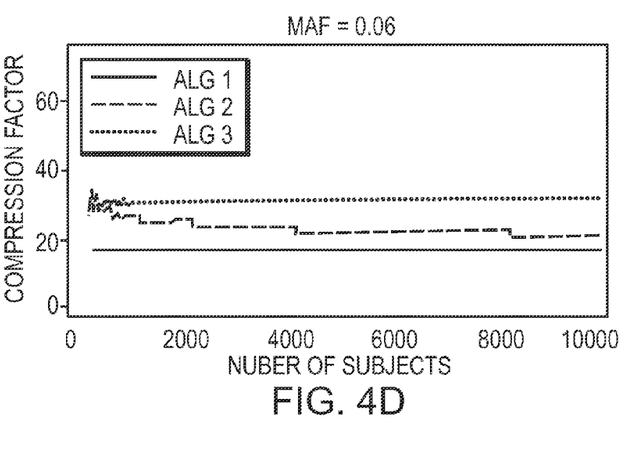
Figure 4E:
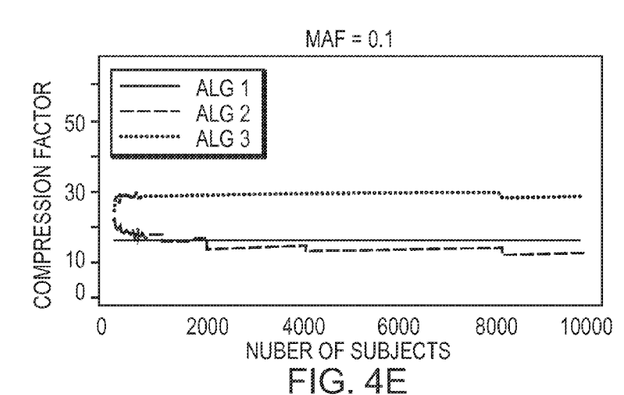
Figure 4F:
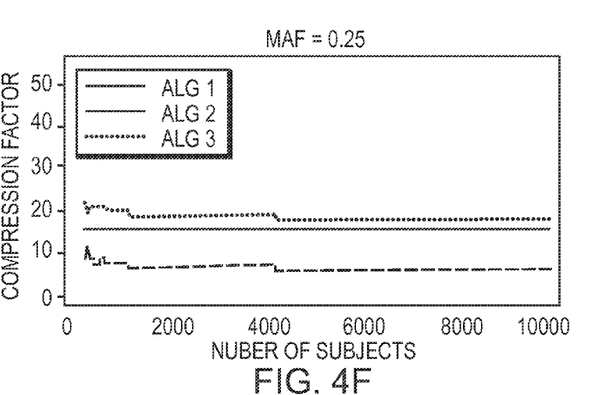
Figure 4G:
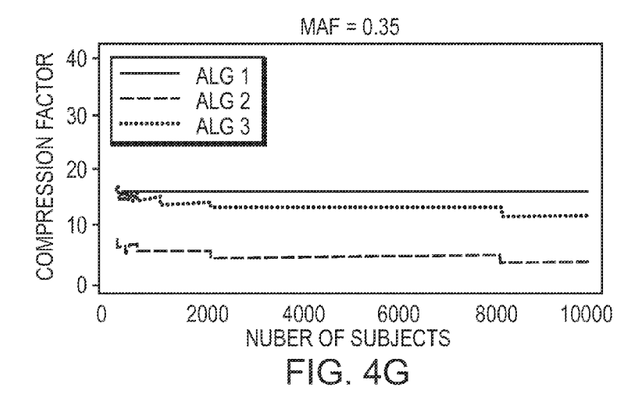
Figure 4H:
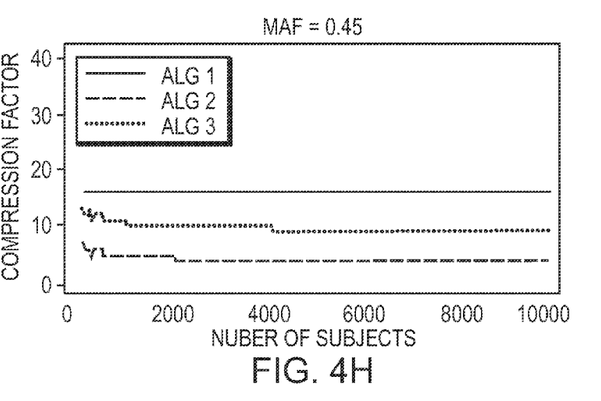

In the binary-encoding algorithm, the genetic information of any marker in one data set is compressed to the same size since the compression algorithm does not depend on the frequency of each genotype. As shown in FIGS. 3A and 3B (explained in more detail below), the performance of the binary compression algorithm (labeled "Alg1") is the best achievable, among the different algorithms compared, when the variants are relatively common (e.g., MAF>30%). However, for SNPs with small MAF, only a few subjects have heterozygous genotypes, and even fewer have the rare homozygous genotype. Thus, it generally wastes disk space to record the genetic information for all subjects, especially for the subjects with the common homozygous genotype, which is by far the most frequent genotype. Accordingly, SNPs with small MAF may be exploited by recording only the indices of the subjects with missing, heterozygous, or rare homozygous genotypes for the SNP. The common homozygous genotype is the default genotype. Since the allele frequency distribution of the human genome is skewed to smaller allele frequencies, the improvements of this approach is usually substantial compared to the binary-encoding algorithm.

Specifically, suppose there are n subjects in the data set. Recording the index of any subject then requires $\log_2(n)$ binary digits. In a first step, the number of the rare homozygous, the heterozygous, and the missing genotypes may be counted. This information may be used to calculate the compressed size and determine whether algorithm II should be used for the SNP. If algorithm II requires the smallest amount of memory, the hybrid algorithm (described below) will select algorithm II for the compression of the genetic data for the SNP. The indices of the subjects with homozygous, heterozygous, and missing genotypes may be transformed into binary digits, and afterwards written into a binary file. Since the numbers of subjects with each genotype are varied, the counts are typically written to the file before the indices of the subjects are output to the file. Thus, the storage requirement of one marker for this algorithm is given by:

$$[\log_2(n) \times (\#Homo+1+\#Heter+1+\#Missing+1)/8] \quad (2),$$

where #Missing, #Homo, and #Heter denote the number of subjects with missing genotype, the number of subjects with the rare homozygous genotype, and the number of subjects with the heterozygous genotype, respectively. Equation (2) is an approximation of the storage requirement, albeit a good one; as with algorithm I, the actual storage requirement is slightly, but typically not substantially, increased due to pedigree information, allele types, and/or padded bits.

2.3 Algorithm III: Compression Using Binary Encoding and Subject Indices

As shown in FIGS. 3A and 3B below, algorithm II (labeled "Alg2") works best for SNPs with very small frequencies, but performs worse than algorithm I for more common SNPs (MAF>30%). However, by combining algorithms I and II, a third approach can be used that performs better than algorithm I and II for SNPs whose allele frequencies are somewhat between "uncommon" and very common. Since the storage space requirement for this third approach can be computed as well, the range for its optimal performance can be computed analytically.

Since the heterozygous genotype is more common for genetic loci that are in the range between "uncommon" and very common, the heterozygous genotype is, in algorithm III, not recorded by an index of subjects. Instead, a binary number of n digits is used to indicate the subjects with heterozygous genotype, where n is the number of subjects in the data set. For example, if subject i has heterozygous genotype for the SNP, "1" may be put at position i instead of "0." In addition, the indices of subjects with missing and homozygous minor allele genotypes may be recorded in the same way as in algorithm II. The storage requirement of one marker for this algorithm is given by:

$$[((\#Homo+1+\#Missing+1) \times \log_2(n)+n)/8] \text{Bytes} \quad (3),$$

where #Homo and #Missing denote the number of subjects with the rare homozygous genotype and the number of subjects with missing genotype for the SNP, respectively. Again, equation (3) is an approximation of the storage requirement; as with algorithms I and II, the actual storage requirements may be slightly higher due to pedigree information, allele types, and/or padded bits.

2.4 Hybrid Compression Method and Performance Comparison

In various embodiments, a hybrid compression method is used to first compute for each genetic locus (or marker) the storage requirements of the three algorithms (e.g., using formulas (1)-(3) above), and then select the algorithm that has the lowest storage requirement for compressing the genetic data for this marker. To assess the performance of the hybrid method, FIGS. 3A and 3B compare the compression factor (i.e., the ratio of storage requirements for data in the standard LINKAGE format to storage requirements for the compressed data) and storage requirements of the hybrid method (labeled "SpeedGene") with those of the individual three algorithms described above (labeled "Alg1," "Alg2," and "Alg3"). The efficiency of algorithms I, II, and III depends generally on two factors: the genotype frequency of the genetic locus and the number of subjects included in the dataset. Assuming Hardy-Weinberg equilibrium, FIG. 3A provides a plot of the compression factors of the three algorithms versus different MAFs of one SNP for a dataset of 1000 subjects. FIG. 3B shows the number of bits needed for storing the information for one genotype for a dataset with 1000 subjects at different MAF values. The original space needed to record this information for one SNP was 4000 Bytes. The dashed line provides the performance for the hybrid method, which is based on the MAF and formulas (1), (2), and (3) to select the optimal compression procedure among algorithms I-III.

As shown in the plot, the hybrid method achieves a compression factor of about 16 (relative to data in standard LINKAGE format) for MAF>0:3, for which the binary-compression algorithm is used. It accomplishes a compression factor between 16 and 30 for 0:05<MAF<0:3, for which algorithm II is selected. For rare and uncommon alleles (MAF<0:05), a compression factor of at least 30 is realized. With smaller MAF, the compression factor increases rapidly. Equivalently, 2 bits per genotype would be needed for MAF>0:3, about 1.0 to 2.0 bits per genotype for 0:05<MAF<0:3, and less than 1 bit per genotype is needed for MAF<0:05.

The performance of the algorithms also depends on the number of subjects in the dataset. FIGS. 4A-4H show the compression factor of the algorithms for one marker for different numbers of subjects, at eight MAF levels. Generally, the compression factor decreases slightly as the number of subjects included increases, but is fairly constant over the range of numbers of subjects that was considered for different values of MAF. FIGS. 4A-4H confirm the information inferred from FIGS. 3A-3B. For example, for SNP with MAF=0:01, algorithm II can compress the genetic information by a factor of at least 100, which is much better than what algorithms I and III can achieve. However, for more common SNPs where 0:05<MAF<0:3, algorithm III is generally better with a compression factor of 20-30. For more common SNPs (MAF>0:3), algorithm I is generally the optimal solution with a compression factor of consistently 16. Thus, MAF is the most influential factor in determining which of algorithms I, II, and III is optimal.

To empirically test the performance of the hybrid algorithm, a particular embodiment thereof, herein referred to as the SpeedGene algorithm, was applied to various datasets; the results are summarized in the following examples.

EXAMPLE 1

The SpeedGene algorithm was applied to three datasets that were genotyped on commonly used GWAS SNP-chips, which have an emphasis on common SNPs. On average, SpeedGene can reach a compression factor between around 17 and around 23 for such datasets; this is equivalent to 1.3-1.8 bits needed per genotype. Details are shown in Table 1:

TABLE 1

| Datasets | Original Size | Compressed Size (PLINK) | Compressed Size (SpeedGene) | Average MAF | Number of SNPs |
|---|---|---|---|---|---|
| HumanHap 550 | 2.425 GB | 155 MB | 141 MB | 0.2398 | 534290 |
| Affymetrix 6.0 | 2.553 GB | 164 MB | 181 MB | 0.2033 | 484422 |
| Affymetrix 6.0 | 4.559 GB | 293 MB | 204 MB | 0.1979 | 909622 |

EXAMPLE 2

The SpeedGene algorithm was also applied to sequence data, for which the MAF are generally very small. Two datasets with 1000 subjects were simulated based on the Wright's distribution, which is $f(p)=cp^{\beta_s-1}(1-p)^{\beta_n-1}e^{\sigma(1-p)}$, where the scaled mutation rates $\beta_s=0.001$, $\beta_n=\beta_s/3$, the selection rate $\sigma=12$, and c is a normalizing constant. Table 2 shows the compressed file size for the simulated sequence data sets. Since, for sequence data, the optimal algorithm is generally algorithm 2, SpeedGene is able to achieve a very large compression factor. In the simulated data, the compression factor is approximately 200, which is equivalent to 0.16 bits per genotype, whereas 2 bits per genotype is required by PLINK or PBAT.

TABLE 2

| Number of SNPs | Original Size | PLINK | SpeedGene | Average MAF |
|---|---|---|---|---|
| 1 million | 3.725 GB | 238 MB | 21 MB | 0.008521 |
| 30 million | 111.759 GB | 6.985 GB | 471 MB | 0.005443 |

EXAMPLE 3

The SpeedGene algorithm was also applied to the third release of the phase I 1000 genome data, which contains genotype calls of 1092 samples for SNPs, short indels, and large deletions. The original data was converted to pedigree files, and the indels and large deletions were removed in the process. The compression rate of SpeedGene was determined for three different populations, for different chromosomes, and for the entire genomes (sex chromosomes are not included) of the 1092 samples. The compressed file size using SpeedGene for three different populations are shown below in Table 3. The three datasets contain the 22 autosomal chromosomes of 97 Han Chinese in Beijing (CHB), 98 Yoruba in Ibadan, Nigera (YRI), and 98 Toscani in Italy (TSI). The compressed file includes the compressed genotypes of 36 million markers, and the table that matches each marker with its position in the file for fast access, which takes about 150 MB. There are less than one hundred subjects in each dataset. With larger number of subjects in each dataset, the compression rate would increase since the table would take a smaller proportion of the file.

TABLE 3

| Population | CHB | YRI | TSI |
|---|---|---|---|
| Original File Size | 13.89 GB | 12.38 GB | 14.02 GB |
| Compressed File Size | 447 MB | 482 MB | 457 MB |
| Average MAF | 0.03754 | 0.05041 | 0.04015 |

SpeedGene was also applied to each chromosome separately. The results of two chromosomes are shown in Table 4; the compression rates are similar for the chromosomes. Each dataset contains 1092 samples.

TABLE 4

| Data | Chromosome 1 | Chromosome 10 |
|---|---|---|
| Original File Size | 11.78 GB | 7.41 GB |
| Compressed File Size | 172.18 MB | 111.34 MB |
| Average MAF | 0.04419 | 0.04619 |

3. Implementation

The compression methods and algorithms described herein may be implemented by computer-executable instructions, such as program modules, that are executed by a conventional computer. Generally, program modules include routines, programs, objects, components, data structures, etc. that perform particular tasks or implement particular abstract data types. Those skilled in the art will appreciate that the invention may be practiced with various computer system configurations, including multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote computer-storage media including memory storage devices.

Communication in the network can take place via a wireless link (such as, e.g., a wireless a local area network (LAN), a wide area network (WAN), or a wireless personal area), or, alternatively, via a wired link. When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Computers may be connected over the Internet, an Intranet, Extranet, Ethernet, or any other system that provides communications. Suitable communications protocols include, for example, TCP/IP, UDP, or OSI. For wireless communications, communications protocols may include Bluetooth, Zigbee, IrDa or another suitable protocol. Furthermore, components of the system may communicate through a combination of wired or wireless paths.

A central computing device in a distributed computing environment, or a stand-alone computer, may comprise or consist of a general-purpose computer including a processing unit, a system memory, and a system bus that couples various system components including the system memory to the processing unit. Computers typically include a variety of computer-readable media that can form part of the system memory and be read by the processing unit. By way of example, and not limitation, computer readable media may comprise computer storage media and communication media. The system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RAM typically contains data and/or program modules that are immediately accessible to and/or presently being operated on by processing unit. The data or program modules may include an operating system, application programs, other program modules, and program data. The operating system may be or include a variety of operating systems such as Microsoft WINDOWS operating system, the Unix operating system, the Linux operating system, the Xenix operating system, the IBM AIX operating system, the Hewlett Packard UX operating system, the Novell NETWARE operating system, the Sun Microsystems SOLARIS operating system, the OS/2 operating system, the BeOS operating system, the MACINTOSH operating system, the APACHE operating system, an OPENSTEP operating system or another operating system of platform.

The computing environment may also include other removable/nonremovable, volatile/nonvolatile computer storage media. For example, a hard disk drive may read or write to nonremovable, nonvolatile magnetic media. A magnetic disk drive may read from or writes to a removable, nonvolatile magnetic disk, and an optical disk drive may read from or write to a removable, nonvolatile optical disk such as a CD-ROM or other optical medium. Other removable/nonremovable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The storage media are typically connected to the system bus through a removable or non-removable memory interface.

The processing unit that executes commands and instructions may be a general-purpose processor, but may utilize any of a wide variety of other technologies including special-purpose hardware, a microcomputer, mini-computer, mainframe computer, programmed micro-processor, microcontroller, peripheral integrated circuit element, a CSIC (Customer Specific Integrated Circuit), ASIC (Application Specific Integrated Circuit), a logic circuit, a digital signal processor, a programmable logic device such as an FPGA (Field Programmable Gate Array), PLD (Programmable Logic Device), PLA (Programmable Logic Array), RFID processor, smart chip, or any other device or arrangement of devices that is capable of implementing the steps of the processes of the invention.

Any suitable programming language may be used to implement without undue experimentation the functions described above. Illustratively, the programming language used may include assembly language, Ada, APL, Basic, C, C++, C*, COBOL, dBase, Forth, FORTRAN, Java, Modula-2, Pascal, Prolog, Python, REXX, and/or JavaScript for example. Further, it is not necessary that a single type of instruction or programming language be utilized in conjunction with the operation of the system and method of the invention. Rather, any number of different programming languages may be utilized as is necessary or desirable.

In certain embodiments, the functionality of compression methods in accordance herewith is implemented in a C++ library, which makes it straightforward for users to incorporate it into their own programs. New files that are created by the compression algorithms can be directly loaded with the library. The user can retrieve the information that was stored in the original pedigree file and the summarized marker information. The C++ library may include two classes. The first class may be responsible for compressing a pedigree file in the LINKAGE format into a text file that contains the pedigree information only, and a binary file that contains the compressed genetic information. More specifically, the first class may include a function for reading the original pedigree file, writing the pedigree information into a separate text file, and storing the marker information in memory. This information is then used to determine the minor and major alleles and the numbers of subjects with homogenous, heterogeneous, and missing genotypes, from which the storage requirements for the three algorithms described above are computed. The hybrid algorithm then compresses the marker information with the respective optimal algorithm into a binary file, which is not human-readable.

The second class may be responsible for loading the compressed binary files into memory, and for processing queries from the user. The user may, for example, retrieve information for specific markers or specific identified subjects, or a listing of all subjects having a particular genotype for one marker. The selective retrieved genetic data may be displayed along with the pedigree information for the subjects. Further, multiple sections of the file that correspond, e.g., to respective subsets of the marker may be loaded in parallel into different memories for simultaneous processing by multiple parallel processors. For many purposes (including the types of user queries mentioned above), the compressed data may be used without decompression. (In some embodiments, the compressed data is stored in binary format and, upon loading into memory, translated into an integer array; this does not constitute decompression.) However, if desired, the original genotype data (except for the allele type of a marker for which the second allele type is unknown) may be restored from the compressed files, as long as the major and minor allele types for each marker are stored. Thus, any standard, conventional genome analysis that relies only on genotype data can be performed on the data (with or without decompression, depending on the particular analysis).

Figure 5:
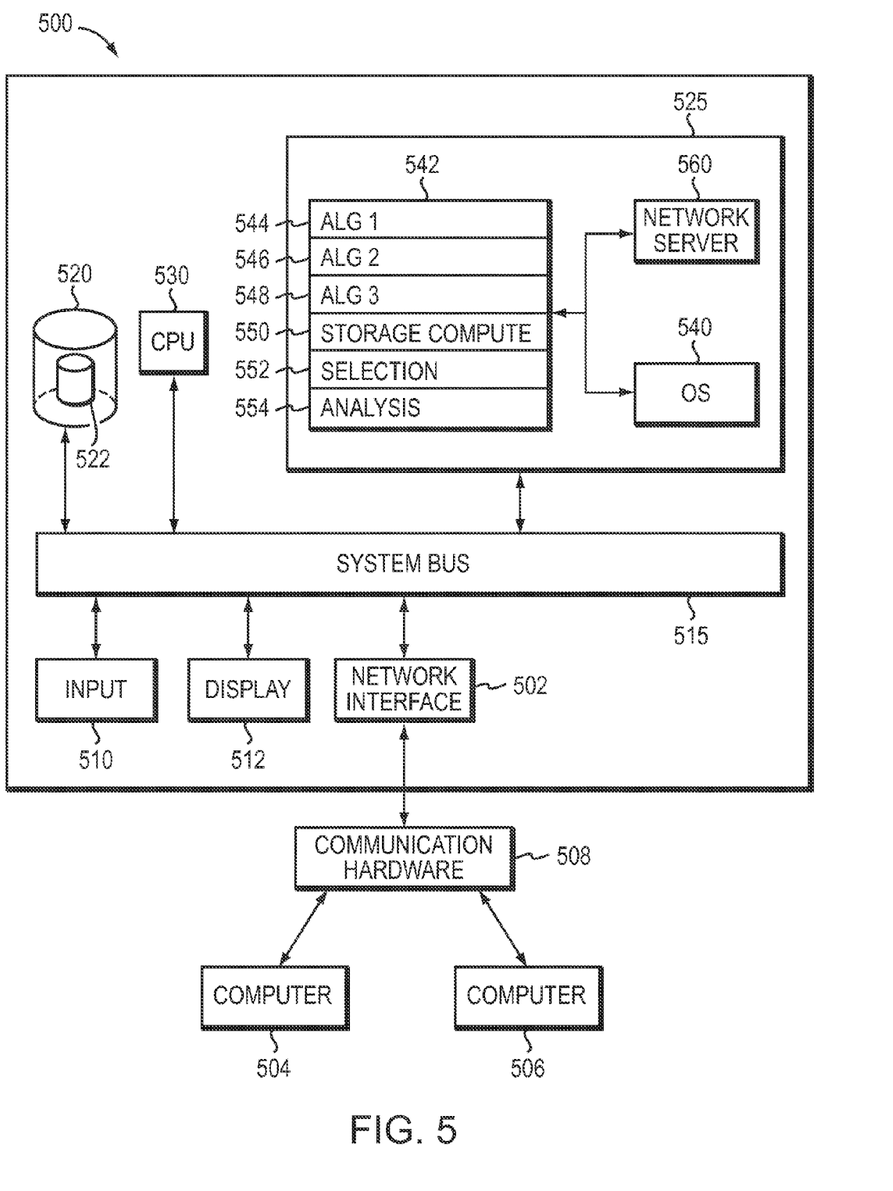
FIG. 5 is a block diagram of a computer system in accordance with various embodiments.

FIG. 5 illustrates, in block-diagram form, an exemplary computer 500 with features enabling it to perform genetic-data compression and storage in accordance herewith, as well as its integration into a network. The computer 500 includes a network interface 502, which interacts with other computers 504, 506 of the network via communication hardware 508. The computer 100 also includes input devices 510 (e.g., a keyboard, a mouse or other position-sensing device, etc.), by means of which a user can interact with the system, and a screen display 512. The computer 500 further includes a bidirectional system bus 515, over which the system components communicate, a non-volatile mass storage device (such as one or more hard disks and/or optical storage units) 520, which can contain one or more databases 522, and a main (typically volatile) system memory 525. The operation of computer 500 is directed by a central-processing unit ("CPU") 530.

The main memory 525 contains instructions, conceptually illustrated as a group of modules, that control the operation of CPU 530 and its interaction with the other hardware components. An operating system 540 directs the execution of low-level, basic system functions such as memory allocation, file management and operation of mass storage devices 520. At a higher level, one or more service applications 542 carry out the genetic-data compression in accordance with various embodiments. The service applications 542 may include three compression modules 544, 546, 548 for compressing genetic data (received, e.g., in LINKAGE format) in accordance with algorithms I, II, and III, respectively; a storage computation module 550 for computing the storage requirements associated with each of the three algorithms; and a selection module 552 that determines for each marker, based on the computed storage requirements, which of the three algorithms to use to compress the data. Further, a query and analysis module 554 may be provided, which can load the compressed data into system memory 525, receive requests from users (e.g., through I/O devices 110), and process the data in response to the requests and/or perform standard genome analysis.

The compressed genetic data may be stored on mass storage devices 520, e.g., within the database 522. Alternatively or additionally, the data may be sent to other computers 504, 506 of the network. Similarly, the original genetic data to be compressed may be loaded into system memory 525 from mass storage devices 520, or received either from another application of computer 500, or from other computers 504, 506 of the network. To enable the handling of requests from computers 504, 506, the main memory 525 contains a network-server block 560. If the network is the Internet, for example, block 550 can be a conventional web server application.

The algorithms described herein are generally applicable in any scenario in which multiple genomes are stored in the computing environment. The genomes need not necessarily come from the same study. Further, data for a new genome sequence can readily be added to an existing archive in a manner that provides the compression benefits. Moreover, sequence data for any individual can readily be retrieved from the compressed data, and such retrieval does not require processing time for decompression, as would be necessary if the data had been compressed using one of various prior-art methods.

While particular embodiments of the invention have been illustrated and described in detail herein, it should be understood that various changes and modifications might be made to the invention without departing from the scope and intent of the invention. Further, it will be understood that certain features and sub-combinations are of utility and may be employed without reference to other features and sub-combinations. This is contemplated and within the scope of the invention.

The invention claimed is:

1. A computer-implemented method of compressing, for a plurality of subjects, genetic data corresponding to at least one bi-allelic marker having at least one minor allele frequency associated therewith, the method utilizing at least two compression algorithms and comprising:
    for each of the at least one bi-allelic marker,
        using a computer processor to (i) compute storage requirements associated with each of the at least two compression algorithms, the storage requirement of at least one of the compression algorithms depending, at least in part, on the minor allele frequency associated with the marker, and (ii) compress the genetic data for the marker using only the compression algorithm having the lowest storage requirement associated therewith, and
        storing the compressed genetic data; and
    using the computer processor, analyzing the compressed genetic data without decompression,
    wherein the at least two compression algorithms are selected from (i) a binary-encoding algorithm, (ii) an algorithm wherein total numbers and unique indices of (a) all subjects having a rare homozygous genotype for a marker, (b) all subjects having a heterozygous genotype for the marker, and (c) all subjects having an unknown genotype for the marker are expressed in binary numbers, and (iii) an algorithm wherein the total numbers and unique indices of (a) all subjects having a rare homozygous genotype for a marker and (b) all subjects having an unknown genotype for the marker are expressed in binary numbers, and the unique indices of all subjects having a heterozygous genotype for the marker are expressed in a single n-digit number, where n is the number of subjects.

2. The method of claim 1, wherein the at least two compression algorithms comprise three compression algorithms.

3. The method of claim 2, wherein the three compression algorithms comprise (i) the binary-encoding algorithm, (ii) the algorithm wherein total numbers and unique indices of (a) all subjects having a rare homozygous genotype for a marker, (b) all subjects having a heterozygous genotype for the marker, and (c) all subjects having an unknown genotype for the marker are expressed in binary numbers, and (iii) the algorithm wherein the total numbers and unique indices of (a) all subjects having an rare homozygous genotype for a marker and (b) all subjects having an unknown genotype for the marker are expressed in binary numbers, and the unique indices of all subjects having a heterozygous genotype for the marker are expressed in a single n-digit number, where n is the number of subjects.

4. The method of claim 1, wherein the storage requirements further depend on the number of subjects.

5. The method of claim 1, wherein analyzing the loaded data comprises processing a user query based thereon.

6. The method of claim 1, wherein the compressed genetic data is stored in binary format on a non-volatile data-storage medium, the method further comprising, prior to analyzing the compressed genetic data, loading the compressed genetic data into memory and converting it into integer format.

7. The method of claim 1, wherein the genetic data, prior to compression, is stored in ASCII format.

8. A computer system for compressing genetic data, the system comprising:
    at least one data storage medium for storing (i) original genetic data for a plurality of subjects, the data corresponding to at least one bi-allelic marker having at least one minor allele frequency associated therewith, and (ii) compressed genetic data; and
    a computer processor, in communication with the at least one data storage medium, for (i) computing, for each of the at least one bi-allelic marker, computer storage requirements associated with each of at least two compression algorithms, the storage requirement of at least one of the compression algorithms depending, at least in part, on the minor allele frequency associated with the marker, and (ii) compressing the genetic data for each of the at least one bi-allelic markers using only the compression algorithm having the lowest storage requirement associated therewith,
    wherein:
        the computer processor is further configured to analyze the compressed genetic data without decompression; and
        the at least two compression algorithms are selected from (i) a binary-encoding algorithm, (ii) an algorithm wherein total numbers and unique indices of (a) all subjects having a rare homozygous genotype for a marker, (b) all subjects having a heterozygous genotype for the maker, and (c) all subjects having an unknown genotype for the marker are expressed in binary numbers, and (iii) an algorithm wherein the total numbers and unique indices of (a) all subjects having an rare homozygous for a marker and (b) all subjects having an unknown genotype for the marker are expressed in binary numbers, and the unique indices of all subjects having a heterozygous genotype for the marker are expressed in a single n-digit number, where n is the number of subjects.

9. The system of claim 8, wherein the computer processor is further configured to process a user query based on the loaded data.

10. The system of claim 8, wherein the compressed genetic data is stored in binary format on the at least one data-storage medium and the computer processor is further configured to load the compressed genetic data into memory and convert the binary format into integer format prior to analyzing the compressed genetic data.

11. The system of claim 8, wherein:
the computer processor is configured to compute, for each of the at least one bi-allelic marker, computer storage requirements associated with three compression algorithms; and
the three compression algorithms comprise (i) the binary-encoding algorithm, (ii) the algorithm wherein total numbers and unique indices of (a) all subjects having a rare homozygous genotype for a marker, (b) all subjects having a heterozygous genotype for the marker, and (c) all subjects having an unknown genotype for the marker are expressed in binary numbers, and (iii) the algorithm wherein the total numbers and unique indices of (a) all subjects having en rare homozygous genotype for a marker and (b) all subjects having an unknown genotype for the marker are expressed in binary numbers, and, the unique indices of all subjects having a heterozygous genotype for the marker are expressed in a single n-digit number, where n is the number of subjects.

* * * * *

UNITED STATES PATENT AND TRADEMARK OFFICE
CERTIFICATE OF CORRECTION

PATENT NO.        : 9,519,650 B2                                    Page 1 of 1
APPLICATION NO.   : 14/131084
DATED             : December 13, 2016
INVENTOR(S)       : Lange et al.

It is certified that error appears in the above-identified patent and that said Letters Patent is hereby corrected as shown below:

In the Claims

Claim 8, Column 15, Line 6, after "homozygous" insert --genotype--;

Claim 11, Column 16, Line 13, change "en" to --an--.

Signed and Sealed this
Second Day of May, 2017

Michelle K. Lee
*Director of the United States Patent and Trademark Office*